(12) United States Patent
Kramer et al.

(10) Patent No.: US 9,662,304 B1
(45) Date of Patent: May 30, 2017

(54) SUBSTITUTED GLUTAURINE COMPOUNDS AND SUBSTITUTED GLUTAURINE DERIVATIVES

(71) Applicant: ThermoLife International, LLC, Phoenix, AZ (US)

(72) Inventors: Ronald Kramer, Phoenix, AZ (US); Alexander Nikolaidis, New Kallikratia (GR)

(73) Assignee: ThermoLife International, LLC, Phoenix, AZ (US)

( * ) Notice: Subject to any disclaimer, the term of this patent is extended or adjusted under 35 U.S.C. 154(b) by 0 days.

(21) Appl. No.: 14/028,872

(22) Filed: Sep. 17, 2013

Related U.S. Application Data

(63) Continuation-in-part of application No. 13/917,045, filed on Jun. 13, 2013.

(51) Int. Cl.
*A61K 31/198* (2006.01)
*A61K 45/06* (2006.01)

(52) U.S. Cl.
CPC ............ *A61K 31/198* (2013.01); *A61K 45/06* (2013.01)

(58) Field of Classification Search
CPC .............................. A61K 31/198; A61K 45/06
See application file for complete search history.

(56) References Cited

PUBLICATIONS

National Institutes of Health NIH Publication No. 07-4191 Updated Apr. 2013.*
Sherman et al. N Engl J Med 2008; 359:31-42.*
Bissantz et al (J. Med. Chem. 2010, 53, 5061-5084).*
Philippe Ducor (Santa Clara High Technology Law Journal, vol. 13 Issue 1, 1997).*
Bittner et al., Glutamyltaurine, Review Article; Amino Acids (2005) 28: 343-356, DOI 10.1007/s00726-005-0196-7; Published online Apr. 21, 2005; # Springer-Verlag 2005.

* cited by examiner

*Primary Examiner* — Savitha Rao
*Assistant Examiner* — Angela Brown-Pettigrew
(74) *Attorney, Agent, or Firm* — Booth Udall Fuller, PLC

(57) ABSTRACT

The present invention is directed to compositions and dietary supplements comprising the following compound

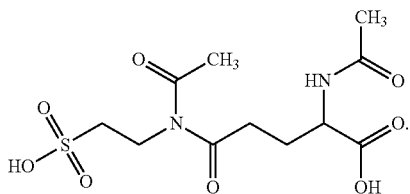

16 Claims, No Drawings

SUBSTITUTED GLUTAURINE COMPOUNDS AND SUBSTITUTED GLUTAURINE DERIVATIVES

CROSS-REFERENCE TO RELATED APPLICATIONS

The present application claims priority to and is a Continuation-In-Part of U.S. patent application Ser. No. 13/917,045 filed Jun. 13, 2013, which is hereby incorporated by reference in its entirety.

TECHNICAL FIELD

The present disclosure relates to compounds and therapeutic compositions for the treatment of a body weight condition, a thyroid disorder, or a disease or condition that is estrogen sensitive, estrogen receptor dependent or estrogen receptor mediated.

BACKGROUND

The principal function of the thyroid gland is to produce the hormones thyroxine (tetraiodothyronine, T4) and tri-iodothyronine (T3), both of which play essential roles in regulating intermediary metabolism in virtually all tissues and in maturation of the nervous system, skeletal muscle and lungs in the developing fetus and the newborn (Werner and Ingbar, The Thyroid: A fundamental and clinical text (Braverman and Utiger, eds.) (1991) pp. 1-1362, Lippincott, Philadelphia; DeGroot, Endocrinology (DeGroot, ed.) (1995) Grune and Stratton, Orlando, Fla.). T3 and T4 are unique hormones in that both contain iodine as an essential constituent.

The hormone-producing thyroid follicular cells or thyrocytes display a highly specialized ability to transport iodide, the anionic form of iodine. This ability is an apparent cellular adaptation to sequester environmentally scarce iodine, thus ensuring adequate thyroid hormone production in most cases. Nevertheless, insufficient dietary supply of iodine is still prevalent among millions of people in many regions of the world, leading to endemic iodine deficiency disorders (IDD) often associated with lower-than-normal thyroid hormone production (Medeiros-Neto, et al., Thyroid Research, (Robbins and Braverman, eds.), (1976) p. 497, Excerpta Medica, Amsterdam).

Administering thyroidal compounds is a common way of treating thyroid disorders and can also increase metabolism, energy expenditure, and fat loss while promoting healthy weight and proportion of lean body mass to adipose tissue. A major disadvantage of thyroidal compounds such as T3,T4, and diiodothyronine is the atrophy they cause to the thyroid gland due to negative feedback. This results in the diminishing of their effectiveness over time as the body's endogenous production lowers. Compounds that increase T3 and T4 levels without causing thyroidal atrophy and compounds that can prevent or reverse thyroidal atrophy are desirable.

Estrogen is a steroid hormone that, while having important functions including the control of reproduction and the development of secondary sexual characteristics, also plays a predominant role in breast cancer growth and development. The use of estrogen for its positive effects can also detrimentally result in the stimulation of other tissues, such as those of the breast and uterus, and increase the risk of cancer at these sites.

The estrogen receptor (ER) is a member of a nuclear receptor superfamily consisting of orphan receptors and receptors for classic high-affinity ligands, such as steroid hormones, vitamin D, retinoids, and thyroid hormones. As a ligand inducible transcription factor, the estrogen receptor mediates the activity of endogenous estrogens in the development and function of the female reproductive system, the maintenance of bone mineral density, regulation of blood lipid profile, brain function, cardiovascular health and other physiologic processes. Endogenous estrogens include 17β-estradiol and estrones. ER has been found to have two isoforms, ER-α and ER-β.

Estrogen-Related Receptors (ERRs) are included in the nuclear receptor family and were the first orphan nuclear receptors found through a search for genes encoding proteins related to known nuclear receptors. While it was originally believed that the development and physiological roles of ERRs were quite distant from those of the classic ERs, it has recently been shown that in some cases ERRs can share target genes, coregulatory proteins, ligands, and sites of action with the ERs. See Riggs, L; Hartman, L, Selective Estrogen-Receptor Modulators—Mechanisms of Action and Application to Clinical Practice. *New England Journal of Medicine* 384:7, 2003. Like ER, ERRs are also implicated in breast cancer and other diseases. See Giguere, V, To ERR in the Estrogen Pathway. *Trends in Endocrinology & Metabolism*, 13:220, 2002.

Therapeutic agents that modulate endogenous levels of estrogens and thereby affect activation of the ER and ERRs are desirable to treat diseases that are estrogen sensitive, estrogen receptor dependent or estrogen receptor mediated. These diseases include cancer, obesity, stroke, hormonal disorders, lipid disorders, metabolic disorders, diabetes, osteoporosis, and heart disease.

SUMMARY

The present disclosure provides a compound of Formula (I):

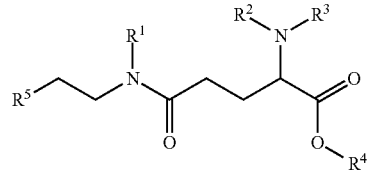

or a salt thereof, wherein each of $R^1$, $R^2$, and $R^3$ independently may be —H, hydrocarbyl, aryl, aralkyl, heteroaryl, heterocyclyl, —C(O)alkyl, —C(O)O(alkyl), —C(O)NH$_2$, —C(O)NH(alkyl), —C(O)N(alkyl)(alkyl), —NHC(O)(alkyl), N(alkyl)C(O)(alkyl), or —SO$_2$NH$_2$;

$R^4$ may be —H, —NH$_2$, —NH(alkyl), —N(alkyl)(alkyl), hydrocarbyl, aryl, aralkyl, heteroaryl, or heterocyclyl;

$R^5$ may be

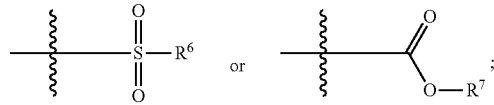

R⁶ may be halo, —OH, —O-hydrocarbyl, —O-aryl, —O-aralkyl, —O-heteroaryl, or —O— heterocyclyl;

R⁷ may be —H, —NH₂, —NH(alkyl), —N(alkyl)(alkyl), hydrocarbyl, aryl, aralkyl, heteroaryl, or heterocyclyl; and the compound or salt thereof is not glutaurine or a salt of glutaurine.

In certain implementations, each of R¹, R², and R³ independently may be —H, hydrocarbyl, or —C(O)alkyl in the compound or salt thereof.

In other implementations, R⁴ may be —H or hydrocarbyl and/or R⁵ may be

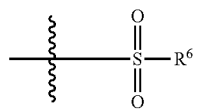

in the compound or salt thereof

The present disclosure also provides a dietary supplement comprising the disclosed compound or salt thereof. The dietary supplement may be formulated to deliver an effective amount of the compound or salt thereof to treat a body weight condition and thereby induce weight and/or fat loss, prevent weight and/or fat gain, and/or increase metabolic consumption of adipose tissue in a subject. In other aspects, the dietary supplement may be formulated to deliver an effective amount of the compound or salt thereof to treat a thyroid disorder and thereby restore normal thyroid function in a subject.

In other implementations, the present disclosure provides a Composition comprising a compound of Formula (I):

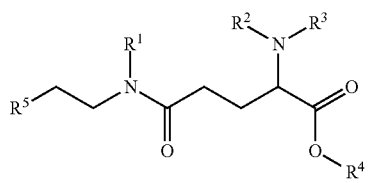

or a salt thereof, wherein each of R¹, R², and R³ independently may be —H, hydrocarbyl, aryl, aralkyl, heteroaryl, heterocyclyl, —C(O)alkyl, —C(O)O(alkyl), —C(O)NH₂, —C(O)NH(alkyl), —C(O)N(alkyl)(alkyl), —NHC(O)(alkyl), N(alkyl)C(O)(alkyl), or —SO₂NH₂;

R⁴ may be —H, —NH₂, —NH(alkyl), —N(alkyl)(alkyl), hydrocarbyl, aryl, aralkyl, heteroaryl, or heterocyclyl;

R⁵ may be

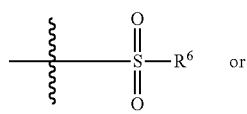 or

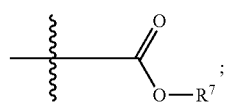;

R⁶ may be halo, —OH, —O-hydrocarbyl, —O-aryl, —O-aralkyl, —O-heteroaryl, or —O-heterocyclyl;

R⁷ may be —H, —NH₂, —NH(alkyl), —N(alkyl)(alkyl), hydrocarbyl, aryl, aralkyl, heteroaryl, or heterocyclyl; and the compound or salt thereof is not glutaurine or a salt of glutaurine.

The Composition may be in a single unit dosage form comprising an effective amount of the compound or salt thereof. In some implementations, the effective amount is from about 1 mcg to about 7,500 mcg.

DETAILED DESCRIPTION

The verbs "comprise" and "include" and their conjugations as used in this description and in the claims are used in their non-limiting sense to mean that items following the words are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some implementations, the subject may be a mammal. In other implementations, the subject may be a human.

As used herein, "Composition" is a term used in its broadest sense and may refer to a mixture of constituent substances or ingredients. "Mixture" is a term used in its broadest sense and may refer to two or more constituent substances or ingredients (chemical species present in a system) which have been combined (not necessarily in fixed proportions and not necessarily with chemical bonding and not necessarily so that each substance retains its own chemical identity). Mixtures can be the product of a blending or mixing of chemical substances like elements and compounds, without chemical bonding or other chemical change, so that each ingredient substance retains its own chemical properties and makeup. Mixtures can be either homogeneous or heterogeneous. A homogeneous mixture is a type of mixture in which the composition is uniform. A heterogeneous mixture is a type of mixture in which the composition can easily be identified, as there are two or more phases present. A homogeneous mixture in which there is both a solute and solvent present is also a solution.

"Compound" and "compounds" as used herein refers to a compound encompassed by the generic formulae disclosed herein, any subgenus of those generic formulae, and any forms of the compounds specified by the generic and subgeneric formulae, such as a salt. The atoms within a compound can be held together by a variety of interactions, ranging from covalent bonds to electrostatic forces in ionic bonds. The physical and chemical properties of compounds are different from those of their constituent elements. This is one of the main criteria for distinguishing a compound from a mixture of elements or other substances because a mixture's properties are generally closely related to and dependent on the properties of its constituents. However, some mixtures are so intimately combined that they have some properties similar to compounds. Another criterion for distinguishing a compound from a mixture is that the constituents of a mixture can usually be separated by simple, mechanical means such as filtering, evaporation, or use of a magnetic force, but the components of a compound can only be separated by a chemical reaction. Conversely, mixtures can be created by mechanical means alone, but a compound can only be created (either from elements or from other compounds, or a combination of the two) by a chemical reaction. Unless specified otherwise, the terms "compound" and "compounds" further includes the isotopes, racemates, stereoisomers, and tautomers of the compound or compounds.

"Isotopes" refer to pharmaceutically acceptable isotopically-labeled compounds wherein one or more atoms are replaced by atoms having the same atomic number, but an atomic mass different from the atomic mass usually found in nature. Suitable isotopes include isotopes of hydrogen, such as 2H and 3H. Substitution with heavier isotopes such as deuterium, i.e. 2H, may afford certain therapeutic advantages resulting from greater metabolic stability, for example, increased in vivo half-life or reduced dosage requirements, and hence may be preferred in some circumstances.

"Racemates" refers to a mixture of enantiomers.

"Solvate" or "solvates" of a compound refer to those compounds, where compounds are as defined herein, that are bound to a stoichiometric or non-stoichiometric amount of a solvent. Solvates of a compound includes solvates of all forms of the compound such as the oxide, ester, prodrug, or pharmaceutically acceptable salt of the disclosed generic and subgeneric formulae. Preferred solvents are volatile, non-toxic, and/or acceptable for administration to humans. The present disclosure provides solvates of the compounds disclosed herein.

"Stereoisomer" or "stereoisomers" refer to compounds that differ in the chirality of one or more stereocenters. Stereoisomers include enantiomers and diastereomers. The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of Advanced Organic Chemistry, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

A "salt" refers to salts derived from a variety of organic and inorganic counter ions well known in the art and includes, by way of example only, sodium, potassium, calcium, magnesium, ammonium, and tetraalkylammonium. When the molecule contains a basic functionality, acid addition salts of organic or inorganic acids, such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, oxalic acid, 4-toluenesulfonic acid, camphorsulfonic acid, methanesulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Salts can also be formed when an acidic proton present in the parent compound is either replaced by a metal ion, e.g., an alkali metal ion, an alkaline earth metal ion, or an aluminum ion; or coordinates with an organic base such as ethanolamine, diethanolamine, triethanolamine, trimethylamine, N-methylglucamine, and the like. Salts are suitable for administration in a subject and possess desirable pharmacological properties. Suitable salts further include those described in P. Heinrich Stahl, Camille G. Wermuth (Eds.), Handbook of Pharmaceutical Salts Properties, Selection, and Use; 2002.

The term "alkyl," as used herein unless otherwise defined, refers to a straight, branched, or cyclic saturated group derived form the removal of a hydrogen atom from an alkane. Representative straight chain alkyl groups include -methyl, -ethyl, -n-propyl, -n-butyl, -n-pentyl, and n-heptyl. Representative branched alkyl groups include -isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl. Representative cyclic alkyl groups include cyclohexyl, cyclopentyl, and cyclopropyl.

The term "alkenyl" refers to a straight, branched, or cyclic hydrocarbon group containing at least one double bond. Representative alkenyl groups include, but are not limited to, ethylene, propylene, 1-butylene, 2-butylene, isobutylene, sec-butylene, 1-pentene, 2-pentene, isopentene, 1-hexene, 2-hexene, 3-hexene and isohexene.

The term "alkynyl" refers to a straight or branched chain hydrocarbon containing at least one triple bond. Representative alkynyl groups include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne and isohexyne.

The term "hydrocarbyl," as used herein unless otherwise defined, refers to a substituent derived from the removal of hydrogen atom from a hydrocarbon molecule. Non-limiting examples of hydrocarbyl include alkyl, alkenyl, alkynyl; cyclic groups consisting of hydrogen and carbon such as aryl as described herein, including both aromatic and non-aromatic groups as described herein; and aralkyl described herein.

The term "aryl" as used herein unless otherwise defined, refers to an aromatic group. Non-limiting examples of aryl include phenyl, naphthyl, pyridyl, phenanthryl, anthryl, furanyl, azolyl, imidazolyl, and indolyl. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless specified otherwise, the aryl is unsubstituted.

The term "heteroaryl" as used herein unless otherwise defined, refers to an aromatic group, wherein the aromatic group contains at least one ring atom that is not carbon. Non-limiting examples of heteroaryl include pyridyl, furanyl, azolyl, imidazolyl, thiophenyl, and indolyl. In one embodiment, the aryl group is substituted with one or more of the following groups: -halo, —O—($C_1$-$C_6$ alkyl), —CN, —COOR', —OC(O)R, —N(R')$_2$, —NHC(O)R' or —C(O)

NHR' groups wherein each R' is independently —H or unsubstituted —C$_1$-C$_6$ alkyl. Unless specified otherwise, the heteroaryl is unsubstituted.

The term "aralkyl" as used herein unless otherwise defined, refers to an alkyl group, which is substituted with an aryl group. Non-limiting examples of an aralkyl group include benzyl, picolyl, naphthylmethyl.

The term "heterocyclyl" as used herein unless otherwise defined, refers to a cyclic group, wherein the cyclic group contains at least one ring atom that is not carbon. Representative examples heterocyclyl group include, but are not limited to, furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl. In one embodiment, the aryl group is substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless specified otherwise, the heterocyclyl is unsubstituted.

The term "alkoxy," as used herein unless otherwise defined, refers to —O-(alkyl), wherein alkyl is as defined above. Representative examples of a C$_1$-C$_6$ alkoxy include, but are not limited to, —OCH$_3$, —OCH$_2$CH$_3$, —OCH$_2$CH$_2$CH$_3$, —OCH(CH$_3$)CH$_3$, —OCH$_2$CH$_2$CH$_2$CH$_3$, —OCH$_2$CH(CH$_3$)CH$_3$, —OCH(CH$_3$)CH$_2$CH$_3$, —OC(CH$_3$)$_3$, —OCH$_2$CH$_2$CH$_2$CH$_2$CH$_3$, —OCH$_2$CH(CH$_3$)CH$_2$CH$_3$, —OCH$_2$CH$_2$CH$_2$CH$_2$CH$_3$, and —OCH$_2$CH$_2$CH(CH$_3$)CH$_2$CH$_3$.

The terms "halo" and "halogen," as used herein unless otherwise defined, refers to —F, —Cl, —Br or —I.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

As used herein, the term "glutaurine" refers to a compound of the following structure:

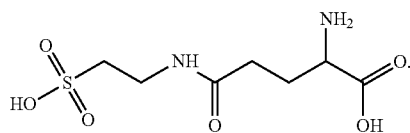 [SMILES: NC(CCC(=O)NCCS(=O)(=O)O)C(=O)O]

Synonymous terms of glutaurine include 5-L-glutamyl-taurine, g-L-glutamyltaurine, L-glutamine, N-(2-sulfoethyl)-N-(2-Sulfoethyl)-L-glutamine, N5-(2-Sulfoethyl)-L-glutamine, γ-glutamyltaurine, γ-L-glutamyltaurine, 5-glutamyltaurine, glutaurin, and Litoralon.

In some implementations, the present disclosure provides a compound of Formula (I):

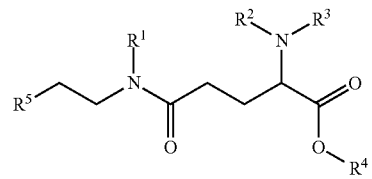

or a salt thereof, wherein each of R$^1$, R$^2$, and R$^3$ independently may be —H, hydrocarbyl, aryl, aralkyl, heteroaryl, heterocyclyl, —C(O)alkyl, —C(O)O(alkyl), —C(O)NH$_2$, —C(O)NH(alkyl), —C(O)N(alkyl)(alkyl), —NHC(O)(alkyl), N(alkyl)C(O)(alkyl), or —SO$_2$NH$_2$;

R$^4$ may be —H, —NH$_2$, —NH(alkyl), —N(alkyl)(alkyl), hydrocarbyl, aryl, aralkyl, heteroaryl, or heterocyclyl;

R$^5$ may be

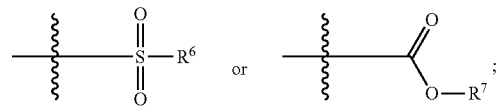

R$^6$ may be halo, —OH, —O-hydrocarbyl, —O-aryl, —O-aralkyl, —O-heteroaryl, or —O— heterocyclyl;

R$^7$ may be —H, —NH$_2$, —NH(alkyl), —N(alkyl)(alkyl), hydrocarbyl, aryl, aralkyl, heteroaryl, or heterocyclyl; and the compound or salt thereof is not glutaurine or a salt of glutaurine.

In specific implementations, the compound or salt thereof may be:

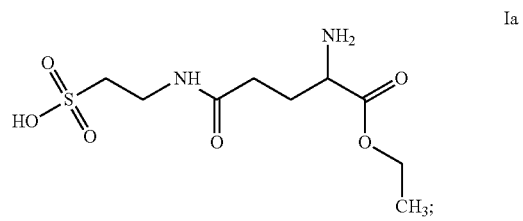

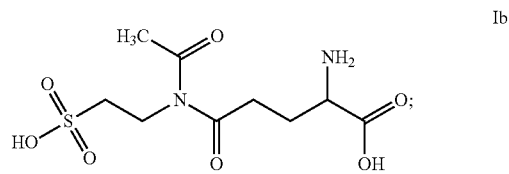

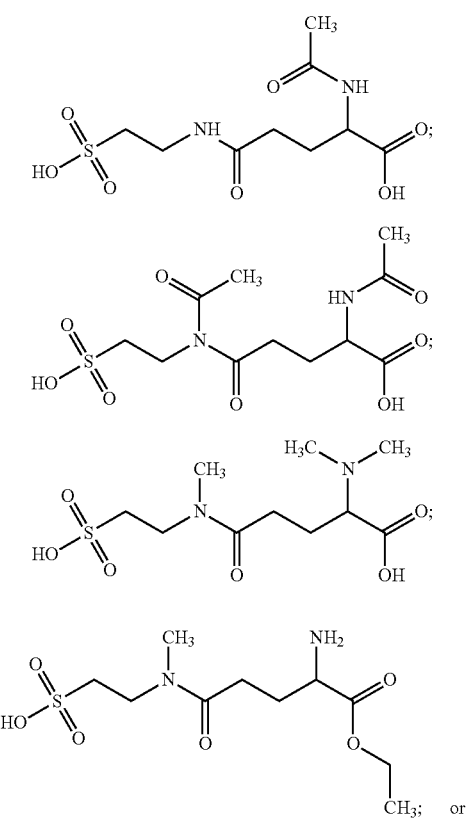

a salt of any of the foregoing.

In other implementations, $R^5$ is

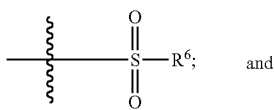

$R^4$ is —H;
$R^6$ is —OH; or
$R^4$ is —H and $R^6$ is —OH in the disclosed compound or salt thereof.

In yet other implementations, $R^5$ is

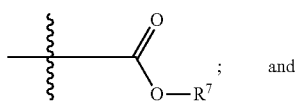

$R^4$ is —H;
$R^7$ is —H; or
$R^4$ is —H and $R^7$ is —H in the disclosed compound or salt thereof.

The compound may be a salt in which at least one acidic proton is replaced with a metal ion. The metal ion may be an alkali metal ion or an alkaline earth metal ion. In certain implementations, the metal ion is potassium, magnesium, or calcium.

As used herein, an "effective amount," an "amount effective for," or "amount sufficient to" is defined as an amount effective, at dosages and for periods of time necessary, to achieve a desired biological result, such as reducing, preventing, or treating a disease or condition and/or inducing a particular beneficial effect. The effective amount of compositions of the disclosure may vary according to factors such as age, sex, and weight of the individual. Dosage regime may be adjusted to provide the optimum response. Several divided doses may be administered daily, or the dose may be proportionally reduced as indicated by the exigencies of an individual's situation. As will be readily appreciated, a composition in accordance with the present disclosure may be administered in a single serving or in multiple servings spaced throughout the day. As will be understood by those skilled in the art, servings need not be limited to daily administration, and may be on an every second or third day or other convenient effective basis. The administration on a given day may be in a single serving or in multiple servings spaced throughout the day depending on the exigencies of the situation.

The present disclosure relates to the discovery that administration of a glutaurine compound increases T3 levels while decreasing estrogen levels in a subject. This effect on T3 and estrogen levels is observed with administration of surprisingly low amounts of the glutaurine compound. Because of the glutaurine compound's effect on T3 and estrogen levels it can be used to treat thyroid disorders, a body weight condition, and diseases or conditions that are estrogen sensitive, estrogen receptor dependent or estrogen receptor mediated such as breast cancer.

The present disclosure provides a method of treating a body weight condition comprising administering to a subject a composition comprising an effective amount of a disclosed compound or salt thereof, thereby inducing weight and/or fat loss, preventing weight and/or fat gain, and/or increasing the metabolic consumption of adipose tissue in the subject.

In another aspect, the present disclosure provides a method of treating a disease or condition that is estrogen sensitive, estrogen receptor dependent or estrogen receptor mediated comprising administering to a subject a composition comprising an effective amount of a disclosed compound or salt thereof, thereby inducing decreased endogenous levels of estrogen in the subject.

The present disclosure further provides a method of treating a thyroid disorder, comprising administering to a subject a composition comprising an effective amount of a disclosed compound or salt thereof, thereby restoring normal thyroid function in the subject.

In one implementation, the present disclosure provides a method of increasing testosterone levels in a subject comprising administering to a subject a composition comprising an effective amount of a disclosed compound or salt thereof, thereby inducing increased endogenous levels of testosterone in the subject.

In one implementation, the present disclosure provides a method of regulating body weight comprising administering to a subject a disclosed compound or salt thereof in an amount effective to maintain muscle mass while inducing weight and/or fat loss, preventing weight and/or fat gain, and/or increasing the metabolic consumption of adipose tissue in the individual. The method may further comprise maintaining and/or inducing an increase in muscle mass. In one implementation, the composition may be administered to a subject in need thereof to treat obesity. In another implementation, the administration of the composition results in an increased energy expenditure and/or metabolism in the subject.

The retention of lean or muscle mass may be maintained selectively, in various regions of the body, e.g., in skeletal muscle, in the limbs (such as arms and legs) or the trunk. For example, the administration of the compound can maintain gastrocnemius muscle. Likewise, inducement of fat loss may also be selectively targeted in various regions or types, e.g., loss of fat pad mass, abdominal-fat, perirenal fat or subscapular fat and/or combinations. The present disclosure may also assist in inducing fat loss while maintaining lean or muscle mass. Maintaining muscle mass may include gaining at least about 1, 2, 5, or 10% muscle mass, or not losing any muscle mass, or losing no more than about 1%, 2%, or 5% of muscle mass during the period when the compound is administered to the subject.

The present disclosure also provides methods for treating a thyroid disorder in a subject such as hypothyroidism, hyperthyroidism, and thyroid cancer. The thyroid disorder may be associated with reduced or undetectable iodide transport activity in the subject's thyroid cells. The methods and compositions of the present disclosure may be used to support healthy thyroidal hormone levels and good thyroidal function.

In certain aspect, the compositions of the present disclosure induce an increase in T3 levels in a subject while preventing thyroidal atrophy. A negative feedback loop between the thyroid gland, the pituitary, and the hypothalamus maintains the endogenous thyroid hormones at a constant level in adults of higher vertebrates (Larsen P R (1989) Adv Exp Med Biol 261:11-26). Without wishing to be bound to any theory, the compositions of the present disclosure may stimulate T3 production without triggering this negative feedback loop, thus avoiding thyroidal atrophy.

In certain aspects, the compositions of the present disclosure can promote weight loss by increasing thyroidal production levels without negative effects on thyroidal function. The compositions can actually promote thyroid health and prevent other co-administered thyroidal compounds from causing thyroidal atrophy.

The compositions of the present disclosure may be used to treat any disease in which modulating one or more of estrogen levels, the ERs, the ERRs or a combination thereof treats the disease. In another aspect, the present disclosure provides compositions for the treatment of diseases or conditions that are estrogen sensitive, estrogen receptor dependent or estrogen receptor mediated.

In some implementations, the disease or condition may be breast cancer, ovarian cancer, colon cancer, prostate cancer, endometrial cancer, or uterine cancer. In other implementations, the disease or condition may be bone cancer, breast cancer, colorectal cancer, endometrial cancer, prostate cancer, ovarian cancer, uterine cancer, cervical cancer, lung cancer, alcoholism, migraine, aortic aneurysm, susceptibility to myocardial infarction, aortic valve sclerosis, cardiovascular disease, coronary artery disease, hypertension, deep vein thrombosis, Graves' Disease, arthritis, multiple sclerosis, cirrhosis, hepatitis B, chronic liver disease, bone density, cholestasis, hypospadias, obesity, osteoarthritis, osteopenia, osteoporosis, Alzheimer's disease, Parkinson's disease, migraine, vertigo, anorexia nervosa, attention deficit hyperactivity disorder (ADHD), dementia, major depressive disorder, psychosis, age of menarche, endometriosis, or infertility. Additional diseases that may be treated include proliferative disease, obesity, stroke, hormonal disorders, lipidemia and other lipid disorders, metabolic disorders, diabetes, diseases related to fetal development, osteoporosis and heart disease.

In certain aspects, the present disclosure provides a method of increasing testosterone in a subject comprising administering to a subject of a composition comprising a disclosed compound induces increases endogenous levels of testosterone in the subject thereby inducing increased endogenous levels of testosterone in the subject. Administration of the composition may also induce decreased endogenous levels of estrogen in the subject.

Reducing estrogen levels in a subject generally results in increased testosterone levels. Grumbach and Auchus reported that estrogen deficiency in men leads to increased testosterone levels. See Grumbach and Auchus (1999) JCEM 84 (12): 4677. Furthermore, therapeutic agents that reduce estrogen levels commonly increase testosterone levels. Taxel et al. observed that men treated with the aromatase inhibitor, anastrozole, experienced a significant decrease in estradiol and an increase in total testosterone. See Taxel et al. (2001) JCEM 86 (6): 2869. Similarly, the compositions of the present disclosure have the effect of decreasing estrogen levels while increasing testosterone levels.

In some implementations, the effective amount or single unit dosage of the compounds or salts thereof of the present disclosure is about 1 microgram (mcg) to about 7,500 mcg per day; e.g., any range within about 1 mcg to about 7,500 mcg per day such as about 100 mcg to about 3,000 mcg per day or about 500 mcg to about 1,500 mcg per day. In some implementations, the effective amount or single unit dosage of the compounds is about 1 mcg per day, about 25 mcg per day, about 50 mcg per day, about 100 mcg per day, about 200 mcg per day, about 300 mcg per day, about 400 mcg per day, about 500 mcg per day, about 600 mcg per day, about 700 mcg per day, about 800 mcg per day, about 900 mcg per day, about 1,000 mcg per day, about 1,100 mcg per day, about 1,200 mcg per day, about 1,300 mcg per day, about 1,400 mcg per day, about 1,500 mcg per day, about 2,000 mcg per day, about 2,500 mcg per day, about 3,000 mcg per day, about 3,500 mcg per day, about 4,000 mcg per day, about 4,500 mcg per day, about 5,000 mcg per day, about 5,500 mcg per day, about 6,000 mcg per day, about 6,500 mcg per day, about 7,000 mcg per day, or about 7,500 mcg per day. As used herein, the term "about" refers to a +/−10% variation from the nominal value.

In some implementations, the compounds or salts thereof may be administered to a subject in an effective amount or single unit dosage of about 1 mcg of compound per kg of body weight, about 2 mcg of compound per kg of body weight, about 3 mcg of compound per kg of body weight, about 4 mcg of compound per kg of body weight, about 5 mcg of compound per kg of body weight, about 6 mcg of compound per kg of body weight, about 7 mcg of compound per kg of body weight, about 8 mcg of compound per kg of body weight, about 9 mcg of compound per kg of body weight, about 10 mcg of compound per kg of body weight, about 11 mcg of compound per kg of body weight, about 12 mcg of compound per kg of body weight, about 13 mcg of compound per kg of body weight, about 14 mcg of compound per kg of body weight, or about 15 mcg of compound per kg of body weight. These dosages may be administered once a day, twice a day, three times a day, or more frequently if needed. When the dosages are administered more frequently throughout the day, it is contemplated that smaller dosages will generally be used than when a single administration is given in a day. In one implementation, the compounds or salts thereof are administered to a subject in an effective amount or single unit dosage of about 10 mcg of compound per kg of body weight per day resulting in a dose of 0.75 mg/day for the average 75 kg human.

The composition of the present disclosure may further comprise at least one additional therapeutic agent selected from the group consisting of a thyroid hormone, an iodine compound, forskolin, 3,3'-diiodothyroacetic acid, and 3,5-diiodothyroacetic acid. The compositions are formulated appropriately for the intended use. For example, a pharmaceutical formulation for promoting weight loss in adults while maintaining healthy thyroid output includes:
  about 100 mcg Thyroxine (T4);
  about 1 mg Glutaurine; and
  about 200 mcg Iodine (as Magnesium Iodide)
to be taken once daily preferably in the morning.

In another non-limiting example, a nutritional supplement formulation for promoting weight loss in humans while maintaining healthy thyroid output includes:
  about 2000 mcg 3,3'-Diiodothyroacetic Acid;
  about 2000 mcg 3,5-Diiodothyroacetic Acid;
  about 0.5 mg Glutaurine; and
  about 100 mg Forskolin
to be taken once daily preferably in the morning.

In a non-limiting example, a pharmaceutical formulation for treating hypothyroidism includes:
  about 100 mcg Thyroxine (T4) and
  about 1 mg Glutaurine
to be taken once daily.

In another non-limiting example, tablets consisting of about 0.25 mg of a disclosed compound or salt thereof are to be taken as a nutritional supplement once or twice daily with food to promote overall thyroidal health.

The compounds or salts thereof and compositions of the present disclosure can be administered before, concurrent with, or after other optional components such as other active ingredients. In some implementations the nutritional/dietary supplement compositions contains one or more of the following ingredients, generally as an active ingredient:
  Carbohydrates including, but not limited to, isomaltulose, trehalose, maltodextrin, glucose, sucrose, fructose, lactose, amylose, and/or ribose;
  Water soluble vitamins including, but not limited to, Vitamin C, Vitamin B1, Vitamin B2, Vitamin B3, Vitamin B5 (Pantothenic acid), Vitamin B6, Vitamin B12, and/or Vitamin K;
  Minerals including, but not limited to, calcium, sodium, potassium, chromium, vanadium, magnesium, and/or iron (and derivatives) (sometimes in amounts less than the RDA);
  Nutraceutically acceptable stimulants including, but not limited to, methylxanthines (e.g., caffeine) and/or glucuronolactone (and derivatives);
  Nutraceutically acceptable hypoglycemic agents including, but not limited to, alpha-lipoic acid and its derivatives, cinnamon bark, bitter melon extracts, Gymnema sylvestre extracts, corosolic acid, pterostilbene and/or D-pinitol (and derivatives);
  Creatine, glycocyamine, guanidinopropionic acid, creatinol, and cyclocreatine;
  Amino acids, including but not limited to L-Leucine, L-Isoleucine, L-Valine, L-Citrulline, L-Arginine, L-Ornithine, L-Carnitine, L-Tyrosine, L-Aspartic Acid, D-Aspartic Acid, L-Glutamine, and/or their derivatives including but not limited to any salt or ester thereof;
  Adenosine triphosphates and its disodium salt;
  Glycerol and glycerol monostearate;
  Mannitol;
  Sorbitol; and
  Dextrin.

The composition or formulation may include from about 0.5% to about 100% (by weight) of the disclosed compound or salt thereof, from about 5% to about 100% of the disclosed compound or salt thereof, or from about 50% to about 100% of the disclosed compound or salt thereof As used herein, the terms "nutraceutical" and "nutraceutically acceptable" are used herein to refer to any substance that is a food or part of a food and provides medical or health benefits, including the prevention and treatment of disease. Hence, compositions falling under the label "nutraceutical" or "nutraceutically acceptable" may range from isolated nutrients, nutritional or dietary supplements, and specific diets to genetically engineered designer foods, herbal products, and processed foods such as cereals, soups, and beverages. In a more technical sense, the term has been used to refer to a product isolated or purified from foods, and generally sold in medicinal forms not usually associated with foods and demonstrated to have a physiological benefit or provide protection against chronic disease.

As used herein, the term "derivative" can include salts, esters, ethers, amides, azines, imidines, chelates, lactone forms, hydrates, alkylations (e.g., a mono-methylated or poly-methylated variant of the moiety) or complexes of stated chemicals. Such derivatives can also include stereoisomers or structural isomers, so long as the derivative operates similarly and produces the desired effect. Alternatively, the derivative can be a precursor to the stated chemical, which subsequently undergoes a reaction in vivo to yield the stated chemical or derivative thereof. By way of non-limiting example only, ubiquinol is a useful derivative of ubiquinone, and acetyl-L-carnitine is a useful derivative of L-carnitine, ketoisocaproic acid is a useful derivative of L-leucine, and R-dihydrolipoic acid is a useful derivative of R-α-lipoic acid.

The compositions and formulations of the disclosure may contain pharmaceutically, e.g., nutraceutically, acceptable excipients, according to methods and procedures well known in the art. As used herein, "excipient" refers to substances which are typically of little or no therapeutic value, but are useful in the manufacture and compounding of various pharmaceutical preparations and which generally form the medium of the composition. These substances include, but are not limited to, coloring, flavoring, and diluting agents; emulsifying, dispersing and suspending agents, ointments, bases, pharmaceutical solvents; antioxidants and preservatives; and miscellaneous agents. Suitable excipients are described, for example, in Remington's Pharmaceutical Sciences, which is incorporated herein by reference in its entirety. As used herein, "pharmaceutically acceptable excipient" refers to substances added to produce quality tablets, capsules, granulates, or powders, but which do not provide nutritive value. An exemplary (non-exhaustive) list of such excipients includes monoglycerides, magnesium stearate, modified food starch, gelatin, microcryatalline cellulose, glycerin, stearic acid, silica, yellow beeswax, lecithin, hydroxypropylcellulose, croscarmellose sodium, and crosprovidone.

The compositions and formulations according to the present disclosure can further include one or more acceptable carriers. A wide number of acceptable carriers are known in the nutritional supplement arts, and the carrier can be any suitable carrier. The carrier need only be suitable for administration to animals, including humans, and be able to act as a carrier without substantially affecting the desired activity of the composition. Also, the carrier(s) may be selected based upon the desired administration route and dosage form of the composition. For example, the nutritional supplement compositions according to the present disclosure are suitable for use in a variety of dosage forms, such as liquid form and solid form (e.g., a chewable bar or wafer). In desirable implementations, as discussed below, the nutritional supplement compositions include a solid dosage form, such as a tablet or capsule. The tablet forms can include uncoated tablets, single-layer, multi-layer or encased forms, enteric coated tablets or effervescent tablets. Examples of suitable carriers for use in tablet and capsule compositions include, but are not limited to, organic and inorganic inert carrier materials such as gelatin, starch, magnesium stearate, talc, gums, silicon dioxide, stearic acid, cellulose, and the like. Desirably, the carrier is substantially inert, but it should be noted that the nutritional supplement compositions of the present disclosure may contain further active ingredients in addition to the disclosed compound. In certain aspects the composition or formulation is DSHEA-compliant (i.e., complies with the Dietary Supplement Health and Education Act of 1994).

Dietary Supplements

The compositions of the present disclosure may be formulated as nutritional or dietary supplements. The term "dietary supplement" means a product that is intended to be ingested in addition to a normal animal diet. Dietary supplements may be in any form, e.g., solid, liquid, gel, tablet, capsule, powder, and the like. Preferably they are provided in convenient dosage forms, e.g., in sachets. Dietary supplements can be provided in bulk consumer packages such as bulk powders, liquids, gels, or oils. Similarly such supplements can be provided in bulk quantities to be included in other food items such as snacks, treats, supplement bars, beverages, and the like.

In one aspect, the compounds and compositions are administered to a subject in a dietary supplement. The dietary supplement can have any suitable form such as a gravy, drinking water, beverage, yogurt, powder, granule, paste, suspension, chew, morsel, treat, snack, pellet, pill, capsule, tablet, sachet, or any other suitable delivery form. The dietary supplement can comprise the compounds or compositions and optional compounds such as vitamins, preservatives, probiotics, prebiotics, and antioxidants. This permits the supplement to be administered to a subject in small amounts, or in the alternative, can be diluted before administration to a subject. The dietary supplement may require admixing with a food composition or with water or other diluent prior to administration to the subject.

The dietary and nutritional supplements of the present disclosure may include a pharmaceutically acceptable additive. The additive may be a carrier, an excipient, a binder, a colorant, a flavoring agent, a preservative, a buffer, a dilutant, and/or combinations thereof Particular implementations of the compositions described herein may also comprise an additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, pharmaceutically acceptable additives may include, by non-limiting example, calcium phosphate, cellulose, stearic acid, croscarmelose cellulose, magnesium stearate, and silicon dioxide.

"Pharmaceutically acceptable" as used herein describes ingredients of a pharmaceutical composition that meet Food and Drug Administration (FDA) standards, United States Pharmacopeial Standards (USP), US Department of Agriculture (USDA) standards for food-grade materials, commonly accepted standards of the nutritional supplement industry, industry standards, botanical standards, or standards established by any individual. These standards may delineate acceptable ranges of aspects of ingredients of a pharmaceutical composition such as edibility, toxicity, pharmacological effect, or any other aspect of a chemical, composition, or preparation used in implementations of a pharmaceutical composition.

Dietary supplements formulated for the sustained release of the disclosed compounds are provided. The dietary supplements may include a food product or a liquid product.

Solid Food Products

A dietary supplement formulated as a food product can be in a solid or an edible suspension. Solid food products may include chewable or edible bars, cookies, biscuits, lozenges, chewing gum, or edible suspensions. In one implementation, the dietary supplement containing the disclosed compound is a solid food product in the form of a high-energy multi-saccharide edible bar containing the substance galactose.

In one implementation, an edible food bar includes a saccharide component including 3 to 37% weight/weight (w/w) galactose, 0.1 to 75% w/w of the disclosed compound or salt thereof, and optional further ingredients selected from amino acids, carbohydrates, fiber and fat, and other ingredients such as creatine and beta-alanylhistidine peptides (e.g. carnosine, anserine, and/or balenine). The amount of galactose can be, for example, 5 to 20% w/w (e.g., 5 to 15% w/w). The saccharide component also can include glucose. In one implementation, equal amounts of glucose and galactose are provided. In another implementation, the amount of galactose is greater than the amount of glucose.

Generally, the disclosed compound may be included with other ingredients to give a bar, drink or other type of food that can be low in glucose and can have a low glycemic index. The use of galactose affords several advantages. For example, galactose is not insulogenic; that is, galactose does not itself induce an insulin response. Thus, its use is associated with less of an insulin response than the equivalent mass of glucose. Products may be used by diabetics or persons who are intolerant to lactose. Galactose can be used rapidly by the liver for synthesis of glycogen or glucose, and it is less likely to cause dental erosion than other sugars.

Some implementations of solid food product compositions containing the disclosed compound incorporate 0.1 to 50% of the disclosed compound. In order to prevent unwanted adverse side effects, it is desired that the disclosed compound exhibits sustained or delayed release from the food product. For example, the disclosed compound thereof may be contained within a food product and separated from any moist ingredients by, for example, formulation in layers. Alternatively, the disclosed compound thereof may be embodied within the matrix of the food itself, wherein the nature of the matrix delays dissolution of the food within the stomach. Additionally, the disclosed compound can be encapsulated as granules or powder in a dry water-impervious shell (e.g., micro-encapsulation) and used in a food product. In this way, the disclosed compound can be slowly released in the stomach by dissolution.

Use of fiber in a food product (e.g., an energy bar) is advantageous because different fiber products influence the release of sugars, affect the binding of various components and advantageously delay digestion. An amount of between 0 to 5% (or more) w/w sugars may be used in a food product containing the disclosed compound. Furthermore, a composition containing the disclosed compound may be absorbed onto the fiber prior to the manufacture of the food product. In this way, the absorption of the disclosed compound into the body may be retarded.

In a layered arrangement, the disclosed compound powder or aggregate may be covered with a hard dry sugar layer. Alternatively or in addition, a chocolate containing layer may be used as a moisture barrier. A compound-containing layer may be provided as a laminar cylindrical layer disposed within the bar as the inner layer. Alternatively or in addition, ingredients such as fiber, nuts and dried fruit may be layered onto the layer containing the disclosed compound to form a laminate. Such a layer may incorporate syrup so as to form a composite-type layer.

In alternative food products, the disclosed compound powder or aggregate may be covered with a hard sugar mixture, chocolate or both to form particles with a mass of 100 to 500 mg. These can be combined with the remaining ingredients to form dispersed units within the matrix, for example, as chocolate chips within a cookie. Such an encapsulated arrangement may incorporate layers as previously described.

Edible Suspensions

In another implementation, dietary supplements containing the disclosed compounds or salts thereof are food products wherein the disclosed compounds or salts thereof are suspended in an edible supporting matrix to form an edible suspension. The term "suspension" is intended to mean compositions containing the disclosed compound as provided herein, include the disclosed compound in solid form (e.g. as crystals, powder or the like), distributed within an edible viscous liquid or semi-liquid, or a solid, supporting matrix, typically such that settling (under the influence of gravity) of the solid compound is inhibited or prevented.

The composition may be provided in solid, liquid or semi-liquid form (e.g. as a drink, soup or yogurt). The disclosed compound may be distributed substantially evenly throughout the supporting matrix (by homogenizing in some manner e.g. by stirring, blending or the like), which may be accomplished manually (e.g. by the consumer) and/or mechanically at the time the composition is prepared.

Conveniently, the food product is an otherwise conventional food product supplemented with the disclosed compound such that disclosed compound becomes suspended in the foodstuff. Examples of foodstuffs that may represent suitable supporting matrices for the composition of the disclosure include spreadable solids such as dairy or cheese spreads, margarines, meat and fish pastes and spreads and the like. Other convenient supporting matrices are those containing sugars or other carbohydrates, such as liquid ("runny") or solid ("set") honey, molasses, syrup (e.g. corn syrup, glucose syrup), treacle or gels of any description, foods made viscous by cooling including ice-cream, and foods made viscous by cooking and baking, e.g. muffins, pies, tarts, cakes, biscuits and cereal flakes.

If desired, the viscosity of the edible matrix and/or the composition as a whole, may be increased by the addition of viscosifiers, gelling agents and the like. Such components are well-known in the food industry and include, for example, plant-derived polysaccharides, gums and the like such as galactomannans, dextrans, guar gum, locust bean gum and so on. Such viscosifiers, gels and the like may form the supporting matrix, if desired. One representative edible matrix includes a gel prepared from concentrated Aloe Vera extract: a smooth creamy paste, which, for example, can be packaged in a squeezable tube.

The composition or dietary/nutritional supplement may include one or more further components to improve its palatability, stability, flavor or nutritive quality. These further components may include electrolytes, vitamins (e.g., vitamin E, vitamin C, thiamin, riboflavin, niacin, vitamin B6, folic acid, vitamin B12, biotin, and pantothenic acid), lipids, carbohydrates (e.g., starch and/or sugars, e.g., glucose, fructose, sucrose, and maltrose), amino acids, trace elements, colorings, flavors, artificial sweeteners, natural health improving substances, anti-oxidants, stabilizers, preservatives, and buffers. The composition may be unflavored or have the normal flavor of the matrix. Alternatively, one or more flavors may be added (e.g. fruit, cheese or fish flavor).

Other ingredients that can be included in the presently disclosed compositions and dietary/nutritional supplements can include, for example, anti-oxidants, alpha-lipoic acid, tocotrienols, N-acetylcysteine, Co-enzyme Q-10, extracts of rosemary such as carnosol, botanical anti-oxidants such as green tea polyphenols, grape seed extract, COX-1 type inhibitors such as resveratrol, ginkgo biloba, and garlic extracts. Other amino acids such as L-cysteine or L-citrulline may be added. Combination with an acetylcholine precurser such as choline chloride or phosphatidylcholine may be desirable, for example, to enhance vasodilation. It is to be understood that such combination therapy constitutes a further aspect of the compositions and methods of treatment provided herein.

Artificial sweeteners which can be used include Aspartame, Acesulfam K, Saccharin and Cyclamate. Almost any desired flavoring can be added such as fruity flavors such as berry, lemon, orange, papaya and grapefruit. Citric acid may be used as an acidulant and citrate (e.g. sodium citrate) as a buffering agent. Also, other natural health improving substances such as Pan D'Arco tea, Ginseng, Suma tea, Ginkgo, bee pollen and myrrh may be added in physiologically active amounts. Preservatives such as potassium benzoate and/or potassium sorbate can be included. Coloring can be included such as cold water soluble colorant such as beta-carotene. Other suitable colorings, however, will be apparent to those skilled in the art. A clouding agent may be included in the composition, if desired, to improve the appearance of the composition.

Mineral and trace elements also can be added in any type or form which is suitable for human consumption. It is convenient to provide the calcium and potassium in the form of their gluconates, phosphates or hydrogen phosphates, and magnesium as the oxide or carbonate, chromium as chromium picolinate, selenium as sodium selenite or selenate, and zinc as zinc gluconate.

Pharmaceutical Compositions

Pharmaceutical compositions can be prepared in individual dosage forms. Consequently, pharmaceutical compositions and dosage forms may include the active ingredients disclosed herein. The notation of "the pharmaceutical agent" signifies the compounds described herein or salts thereof. Pharmaceutical compositions and dosage forms can further include a pharmaceutically acceptable carrier. In one implementation, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, other excipients can be used.

Single unit dosage forms are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. The agent may be administered via a parenteral or oral route, but other routes are contemplated.

The composition, shape, and type of dosage forms will typically vary depending on their route of administration and animal being treated. For example, a parenteral dosage form may contain smaller amounts of one or more of the active ingredients it includes than an oral dosage form used to treat the same disease. These and other ways in which specific dosage forms encompassed by this disclosure will vary from one another will be readily apparent to those skilled in the art. See, e.g., Remington's Pharmaceutical Sciences, 18th ed., Mack Publishing, Easton Pa. (1990) which is incorporated by reference in its entirety.

Typical pharmaceutical compositions and dosage forms include one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water.

The disclosure further encompasses pharmaceutical compositions and dosage forms that include one or more compounds that reduce the rate by which an active ingredient will decompose. Such compounds, which are referred to herein as "stabilizers," include, but are not limited to, antioxidants such as ascorbic acid, pH buffers, or salt buffers.

Compositions for administration herein may form solutions, suspensions, tablets, pills, capsules, gel capsules, liquids sustained release formulations or powders. Compounds of the present disclosure can be administered to a subject in any suitable form using any suitable administration route. In various implementations, the compounds can be administered in a food composition, in a dietary supplement, in a pharmaceutical composition, in a nutraceutical composition, or as a medicament. Similarly, the compounds and compositions can be administered using a variety of administration routes, including oral, intranasal, intravenous, intramuscular, intragastric, transpyloric, subcutaneous, rectal, and the like.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Pharmaceutically acceptable excipients, such as vehicles, adjuvants, carriers or diluents, are conventional in the art. Suitable excipient vehicles are, for example, water, saline, dextrose, glycerol, ethanol, or the like, and combinations thereof. In addition, if desired, the vehicle may contain minor amounts of auxiliary substances such as pH adjusting and buffering agents, tonicity adjusting agents, stabilizers, wetting agents, and emulsifying agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

For parenteral administration, the compounds may be administered as injectable dosages or by continuous intravenous infusion of a solution, suspension or emulsion of the compound in a physiologically acceptable diluent as the pharmaceutical carrier, which can be a sterile liquid, such as water, alcohols, oils, emulsions, and other acceptable organic solvents, with or without the addition of a surfactant and other pharmaceutically acceptable adjuvants. The compounds can also be administered in the form of a depot injection or implant preparation, which may be formulated in such a manner as to permit a sustained release of the active ingredient.

Many methods of synthesis of glutaurine have been described. See, e.g., Bittner, S., et al., γ-L-glutamyltaurine, Amino Acids 28:343-356 (2005).

In certain aspects, the sulfonyl functional group on glutaurine may be esterified or contain a halide. Sulfonyl halide groups, such as sulfonyl chloride, occur when a sulfonyl functional group is singly bonded to a halogen atom. They have the general formula R—SO$_2$—X where X is a halide such as chloride. Generally, they are produced by chlorination of sulfonic acids using thionyl chloride and related reagents. Esterified sulfonyl groups have the general formula R—SO$_2$—OR. Such sulfonate esters are often prepared by alcoholysis of the sulfonyl chlorides: RSO$_2$Cl+R'OH→RSO$_2$OR'+HCl.

This disclosure is further illustrated by the following additional examples that should not be construed as limiting.

Those of skill in the art should, in light of the present disclosure, appreciate that many changes can be made to the specific implementations which are disclosed and still obtain a like or similar result without departing from the spirit and scope of the disclosure.

EXAMPLES

Example 1. Effects of Glutaurine on Thyroid Hormone and Estradiol Levels

To evaluate the effect of administration of glutaurine on estradiol and thyroid hormone levels in a human subject, approximately 800 micrograms (mcg) per day of glutaurine were administered orally to the subject over a period of about one month. At Day 0 prior to administration of the glutaurine and at Day 4 and Day 28 during administration of the glutaurine blood samples were collected and analyzed for the levels of estradiol, thyroid stimulating hormone (TSH), and the thyroid hormones triiodothyronine (T3) and thyroxine (T4). Total amounts of T3 and T4 were measured in the blood samples. Table 1 summarizes the levels of the hormones in the blood samples at each time point.

TABLE 1

Estradiol, TSH, T3, and T4 levels in blood samples collected prior to and during oral administration of glutaurine at approximately 800 mcg/day to a human subject.

|  | Estradiol (pg/mL) | TSH (mIU/L) | T4 (mcg/dL) | T3 (ng/dL) |
|---|---|---|---|---|
| Day 0 | 36 | 3.01 | 8.3 | 91 |
| Day 4 | 32 | 3.28 | 7.9 | 96 |
| Day 28 | 30 | 2.74 | 7.3 | 109 |

Administration of glutaurine resulted in a marked decrease in estradiol levels and a consistent increase in T3 levels in the subject. T4 levels were slightly reduced after glutaurine administration, and no significant change was observed in TSH levels.

The subject reported that during administration of the glutaurine he experienced increased body temperature and increased sweating, which are indicative of rising energy expenditures and increased metabolism. The subject also reported fat loss as a result of the glutaurine administration.

Example 2. Synthesis of Salts of Glutaurine Derivatives with Alkali Metals or Alkaline Earth Metals Salts of glutaurine derivatives with alkali metals and alkaline earth metals are synthesized by mixing the glutaurine derivative with corresponding isomolar quantities of the appropriate alkali or alkaline earth base, such as magnesium hydroxide, in a solution of an appropriate solvent, such as water or alcohol, and then removing the solvent from the mixture by drying under vacuum.

Example 3. Synthesis of Glutaurine Ethyl Ester

Glutaurine ethyl ester is synthesized by mixing glutaurine with an excess of alcohol (i.e., ethanol), adding small quantities of $H_2SO_4$ or another strong acid, and heating the mixture while stirring for about an hour. The mixture then is dried under vacuum and glutaurine ethyl ester is obtained.

Glutaurine Ethyl Ester:

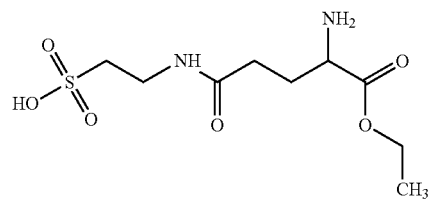 [SMILES: CCOC(=O)C(N)CCC(=O)NCCS(=O)(=O)O]

Example 4. Synthesis of N1,N2-Diacetylglutaurine

N1,N2-diacetylglutaurine is obtained by mixing glutaurine with an excess of acetyl chloride in the presence of pyridine. The mixture is refluxed for 2 hours and N1,N2-diacetylglutaurine is obtained after drying the mixture under vacuum.

N1,N2-Diacetylglutaurine:

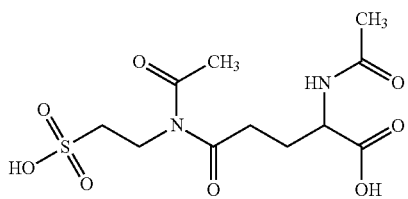 [SMILES: CC(=O)NC(CCC(=O)N(CCS(=O)(=O)O)C(C)=O)C(=O)O]

Example 5. Synthesis of N1-Methyl-N2-Dimethylglutaurine

N1-methyl-N2-dimethylglutaurine is obtained by mixing glutaurine with an excess of methyl iodide ($CHI_3$). The mixture is then refluxed for 6 hours and N1-methyl-N2-dimethylglutaurine is obtained by drying the solution under vacuum.

N1-Methyl-N2-Dimethylglutaurine:

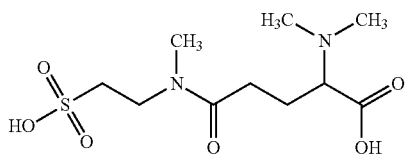 [SMILES: CN(CCS(=O)(=O)O)C(=O)CCC(C(=O)O)N(C)C]

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present disclosure is not entitled to antedate such publication by virtue of prior invention.

It is understood that the disclosed implementations are not limited to the particular methodology, protocols and materials described as these can vary. It is also understood that the terminology used herein is for the purposes of describing particular implementations only and is not intended to limit the scope of the present disclosure which will be limited only by the appended claims.

Those skilled in the art will recognize, or be able to ascertain using no more than routine experimentation, many equivalents to the specific implementations described herein. Such equivalents are intended to be encompassed by the following claims.

What is claimed is:

1. A compound of Formula Id:

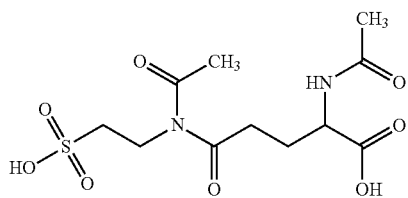 [SMILES: CC(=O)NC(CCC(=O)N(CCS(=O)(=O)O)C(C)=O)C(=O)O]

or a salt thereof.

2. The compound or salt thereof of claim 1, wherein the compound or salt thereof is a salt in which at least one acidic proton is replaced with an alkali metal ion or an alkaline earth metal ion.

3. The compound or salt thereof of claim 1, wherein the compound or salt thereof is a salt in which at least one acidic proton is replaced with a potassium ion, a magnesium ion, or a calcium ion.

4. A dietary supplement comprising the compound or salt thereof of claim 1.

5. The dietary supplement of claim 4, wherein the supplement is formulated to deliver an effective amount of the compound or salt thereof to treat a body weight condition and thereby induce weight and/or fat loss, prevent weight and/or fat gain, and/or increase metabolic consumption of adipose tissue in a subject.

6. The dietary supplement of claim 5, wherein the body weight condition is obesity.

7. The dietary supplement of claim 4, wherein the supplement is formulated to deliver an effective amount of the compound or salt thereof to treat a thyroid disorder and thereby restore normal thyroid function in a subject.

8. The dietary supplement of claim 7, further comprising at least one additional therapeutic agent selected from the group consisting of a thyroid hormone, an iodine compound, forskolin, 3,3'-diiodothyroacetic acid, and 3,5-diiodothyroacetic acid.

9. The dietary supplement of claim 7, wherein the thyroid disorder is selected from the group consisting of hypothyroidism, hyperthyroidism, and thyroid cancer.

10. The dietary supplement of claim 4, wherein the supplement is formulated to deliver an effective amount of the compound or salt thereof to increase testosterone levels in a subject.

11. The dietary supplement of claim 4, wherein the supplement is formulated as a single serving and contains from about 1 mcg to about 7,500 mcg of the compound or salt thereof.

12. The dietary supplement of claim 11, wherein the supplement contains from about 100 mcg to about 3,000 mcg of the compound or salt thereof.

13. The dietary supplement of claim 4, further comprising one or more additional components selected from the group consisting of vitamins, lipids, carbohydrates, amino acids, trace elements, colorings, flavors, artificial sweeteners, natural health improving substances, antioxidants, stabilizers, stimulants, hypoglycemic agents, preservatives, and buffers.

14. The dietary supplement of claim 4, wherein the supplement is formulated in a dosage form selected from the group consisting of a tablet, a chewable tablet, a capsule, a caplet, a lozenge, a troche, an oral gel, a buccal pouch, a granule, a pill, a gel, a bar, a pudding, and a powder.

15. A composition comprising the compound or salt thereof of claim 1, in a single unit dosage form comprising an effective amount of the compound or salt thereof.

16. The composition of claim 15, wherein the effective amount is from about 1 mcg to about 7,500 mcg.

* * * * *